United States Patent [19]

Ross

[11] Patent Number: 5,409,462
[45] Date of Patent: Apr. 25, 1995

[54] CYST PUNCTURE CATHETER ASSEMBLY
[75] Inventor: Donald A. Ross, Ann Arbor, Mich.
[73] Assignee: Cordis Corporation, Miami Lakes, Fla.
[21] Appl. No.: 176,129
[22] Filed: Dec. 30, 1993
[51] Int. Cl.$^6$ ............................................. A61B 17/34
[52] U.S. Cl. ..................................... 604/166; 604/165
[58] Field of Search ............... 604/158, 164, 165, 166, 604/170

[56] References Cited

U.S. PATENT DOCUMENTS

| | | | |
|---|---|---|---|
| 3,540,447 | 11/1970 | Howis | 604/165 |
| 3,896,810 | 7/1975 | Akiyama . | |
| 4,250,881 | 2/1981 | Smith | 604/166 |
| 4,502,482 | 3/1985 | DeLuccia et al. | 604/165 |
| 4,571,239 | 2/1986 | Heyman | 604/165 |
| 4,654,030 | 3/1987 | Moll et al. | 604/165 |
| 4,793,363 | 12/1988 | Ausherman et al. | 604/165 |
| 4,798,591 | 1/1989 | Okada | 604/165 |
| 5,087,080 | 2/1992 | Shutt | 604/165 |
| 5,104,382 | 4/1992 | Brinkerhoff et al. | 604/165 |
| 5,176,647 | 1/1993 | Knoefler | 604/158 |
| 5,201,712 | 4/1993 | Bryant | 604/166 |
| 5,242,427 | 9/1993 | Bilweis | 604/165 |

FOREIGN PATENT DOCUMENTS

| | | | |
|---|---|---|---|
| 150281 | 8/1985 | European Pat. Off. | 604/166 |
| 585840 | 12/1977 | U.S.S.R. | 604/166 |

OTHER PUBLICATIONS

"Treatment of hydrocephalus" by H. L. Rekate, *Pediatric Neurosurgery*, Philadelphia, W. B. Saunders, 1989, pp. 200-218.
"Stereotactic Neurosurgery" by M. Peter Heilbrun, M.D., vol. 2: *Concepts in Neurosurgery*, Baltimore, Williams & Wilkins, 1988, pp. 87-92.
"Stereotactic management of colloid cysts: factors predicting success" by Douglas Kondziolka, M.D. and L. Dade Lunsford, M.D., *J. Neurosurg.* vol. 75, Pittsburg, Jul. 1991, pp. 45-51.
"Stereotactic catheter insertion: A new technique" by Erik-Olof Backlund, Department of Neurosurgery, University of Bergen, Bergen, Norway, *Neurological Research*, Jun. 1987, vol. 9, pp. 147-150.
"Intracystic radiotherapy (90 Y) of Craniopharyngiomas: CT-Guided Stereotaxic Implantation of Indwelling Drainage system" by W. J. Huk and J. Mahistedt, *AJNR*, May/Jun. 1933, pp. 803-806.

*Primary Examiner*—Paul J. Hirsch
*Attorney, Agent, or Firm*—Thomas R. Vigil

[57] ABSTRACT

The cyst puncture catheter assembly comprises: a catheter having a distal portion, a central lumen, an open distal end and a smaller-in-diameter distal end lumen between the central lumen and the open distal end; and, at least one stylet sized to fit within the catheter distal portion. The stylet comprises an elongate shaft having a distal end and a shoulder extending radially outwardly from the shaft at a location close to the stylet distal end. The distal portion of the catheter has an annular shoulder in the central lumen between the central lumen and the smaller-in-diameter lumen against which the shoulder on the stylet can seat so that the stylet and the catheter can be inserted together through tissue to a location of a cyst without the catheter moving longitudinally relative to the stylet.

13 Claims, 1 Drawing Sheet

U.S. Patent    Apr. 25, 1995    5,409,462

CYST PUNCTURE CATHETER ASSEMBLY

BACKGROUND OF THE INVENTION

1. Field of the Invention

The present invention relates to a cyst puncture catheter assembly including a catheter and a stylet wherein the catheter and stylet are inserted into a cyst together without relative movement (telescoping) between the catheter and the needle.

2. Description of the Related Art Including Information Disclosed under 37 C.F.R. §§1.97–1.99

Heretofore, combination cyst puncture stylets and drainage catheters that are inserted into cysts have suffered from the problem of telescoping of the catheter on the stylet when the stylet is inserted into a cyst.

Also, there is a problem in that some cysts can be pierced with a rounded end stylet and other cysts made of a tougher or harder tissue can only be punctured with a pointed end stylet.

In other words, a number of cystic lesions cannot be treated with standard ventricular catheters, as they either have walls too tough to be penetrated by a blunt-ended catheter needle or because they are relatively mobile and are displaced by the catheter rather than punctured by it.

Tough wall cysts may eventually be punctured by a fine sharp biopsy needle but subsequent catheter placement is often difficult or impossible because of drainage of the cyst contents or inability to enter the same hole in the cyst wall with the catheter.

One previously proposed approach to inserting a catheter into a cyst is to first insert a cannula with a sharpened end into the cyst followed by inserting a catheter through the cannula into the cyst. Such a catheter device is disclosed in the Knoepffler U.S. Pat. No. 5,176,647.

A similar structure including a puncture tube that receives a drainage tube therein is disclosed in the Akiyama U.S. Pat. No. 3,896,810.

SUMMARY OF THE INVENTION

The cyst puncture catheter assembly of the present invention includes two stylets, one blunt ended for approaching the cyst and one sharp ended to cut and penetrate the cyst. A specially designed catheter tip is provided that prevents the catheter from telescoping up the stylet as the cyst wall is penetrated. The cyst puncture catheter assembly of the present invention overcomes deficiencies of standard ventricular catheters for the puncture and drainage of difficult intracranial cysts.

Additionally, the cyst puncture catheter assembly of the present invention is especially designed with an open end that makes it easy to use over a biopsy needle when the use of a needle is required to puncture very tough wall cysts.

In all cases, the cyst puncture procedure, and drainage, gains in efficiency and duration. In some cases, cystic lesions, which would have been treated via open surgery (like some of the difficult cases of arachnoid cysts) can be treated under stereotactic guidance using minimal invasive techniques.

Thus, according to the present invention, there is provided a cyst puncture catheter assembly comprising: a catheter having a distal portion, a central lumen, an open distal end and a smaller-in-diameter distal end lumen between the central lumen and the open distal end; and, at least one stylet sized to fit within the catheter distal portion. The stylet comprises an elongate shaft having a distal end and a shoulder extending radially outwardly from the shaft at a location close to the stylet distal end. The distal portion of the catheter has an annular shoulder in the central lumen between the central lumen and the smaller-in-diameter lumen against which the shoulder on the stylet can seat so that the stylet and the catheter can be inserted together through tissue to a location of a cyst without the catheter moving longitudinally relative to the stylet.

DESCRIPTION OF THE PREFERRED EMBODIMENT(S)

Figure 1:
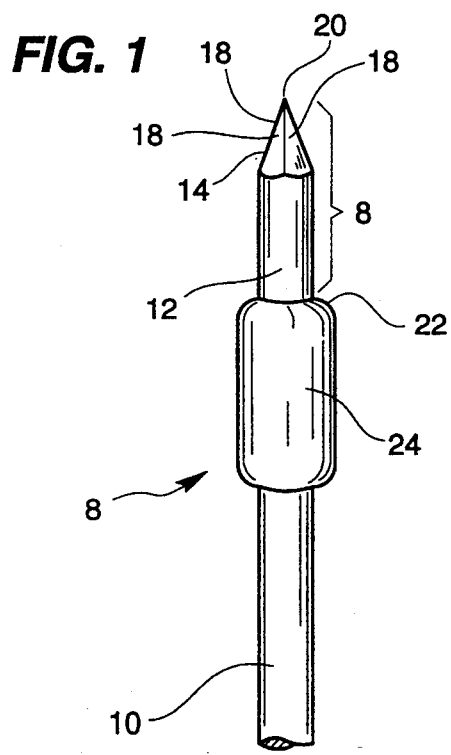
FIG. 1 is a side perspective view of a distal portion of a pointed end stylet constructed according to the teachings of the present invention.

Referring now to the drawings in greater detail, there is illustrated in FIG. 1 a distal portion 8 of a pointed stylet 10 constructed according to the teachings of the present invention. As shown, the stylet 10 has a shaft 12 and a pointed end 14. The pointed end 14 is in the shape of a three or more, e.g. four, sided pyramid 14 so as to have four inclined edges 18 leading to a point 20.

Spaced a short distance proximally of the pointed end 14 on the shaft 12 is an annular shoulder 22. The annular shoulder 22 is located at a distal end of a larger-in-diameter collar or ring 24 formed on and around the shaft 12, such as by machining or by molding techniques.

Figure 2:
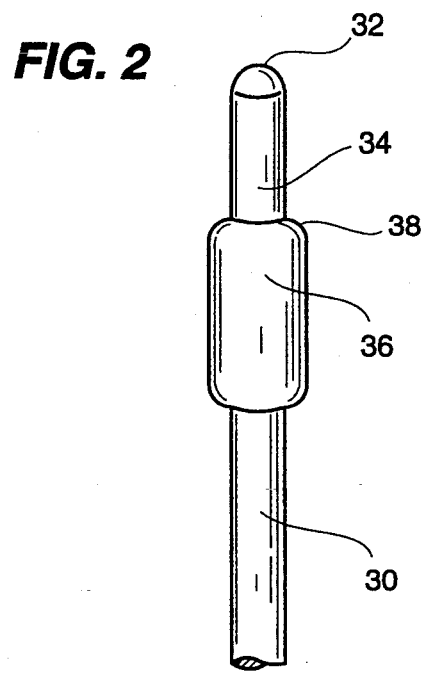
FIG. 2 is a side perspective view of a distal portion of a blunt end stylet constructed according to the teachings of the present invention.

In FIG. 2 is shown a similar stylet 30 which differs from the stylet 10 by having a rounded end 32 instead of a pointed end 14. The rounded end 32 can be partially spherical or hemispherical, as desired. The rounded end stylet 30, like the pointed end stylet 10, has a shaft 34, a larger-in-diameter collar or ring 36 having a distally facing annular shoulder 38.

Figure 3:
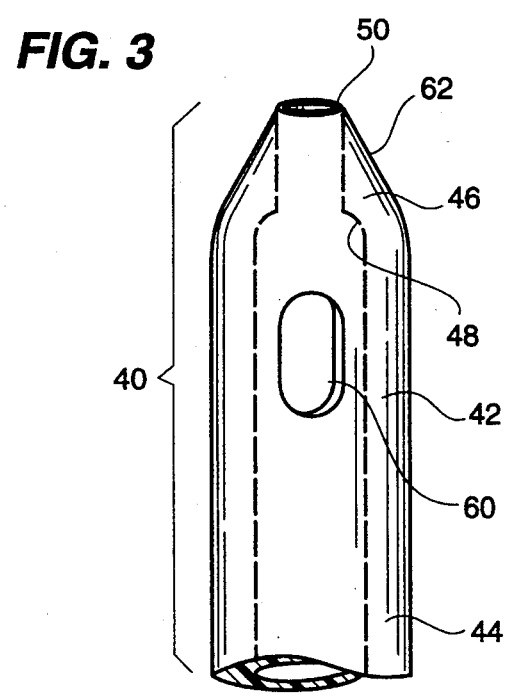
FIG. 3 is a side perspective view of a distal portion of a catheter which is used with the stylets shown in FIGS. 1 and 2.
Figure 4:
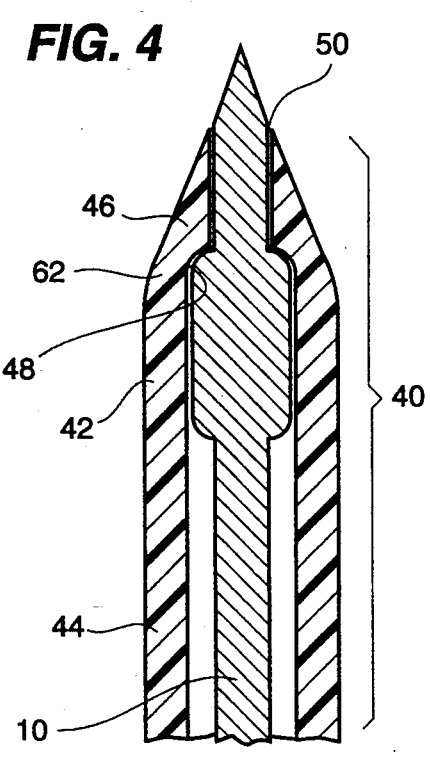
FIG. 4 is a longitudinal sectional view through a distal portion of the stylet shown in FIG. 1 and the catheter shown in FIG. 3 with the stylet positioned within the catheter.

Both of the stylets 10 and 30 are preferably made of stainless steel and are designed to be received into a distal portion 40 of a specially configured catheter 42, shown in FIGS. 3 and 4. The specially configured catheter 42 preferably is made of a silicone elastomer with $BaSO_4$, 0.105 inch×0.056, tubing and has a central lumen 44 of a diameter which corresponds or mates with the outer diameter of the collars 24 or 36 and a smaller-in-diameter distal end lumen 46 having a diameter approximately the same diameter as the shaft 12 or 34. The larger-in-diameter and smaller-in-diameter lumens 44 and 46 are joined by an annular shoulder 48 inside the catheter 42, as shown in FIGS. 3 and 4. The annular shoulder 22 or 38 on collar or ring 24 or 36 is designed to seat against the inner annular shoulder 48 inside the distal portion 40 of the catheter 42.

The smaller-in-diameter lumen or passageway 46 extends from the shoulder 48 to an outer open distal end 50 of the catheter 42. The distance between the inner annular shoulder 48 and the outer open distal end 50 of the smaller-in-diameter lumen 46 is between 2 and 4 millimeters.

Formed in the catheter 42 are two openings 60, which are generally oblong in shape, as shown in FIG. 3 and which are diametrically opposed from each other. These openings 60 are spaced approximately 3 to 6 millimeters from the open distal end 50 of the catheter 42 and have a width of approximately 1 millimeter and a length of approximately 2 millimeters. These openings 60 and the open outer distal end 50 of the catheter 42 form drainage openings once the catheter 42 is inserted into a cyst.

Preferably, and as shown in FIGS. 3 and 4, a distal end 62 of the catheter 42 is rounded, beveled or tapered, to facilitate its insertion through tissue. Preferably, and as shown in FIG. 4, the distal end 62 of the catheter 42 is generally conical in shape and has a taper or incline that mates with the inclined sides of the pyramid shaped pointed end 14 of the stylet 10, thereby to facilitate insertion of the stylet 10 and catheter 42 into a cyst.

Referring now to FIG. 4, there is illustrated therein a cyst puncture catheter assembly 70 including the pointed end stylet 10 received inside the catheter distal end portion 40 ready for insertion into a cyst.

In the use of the cyst puncture catheter assembly 70 shown in FIG. 4, in puncturing and draining a cyst in the brain, a hole is first cut through the skull. Then, a device including a set of guides for stereotactically inserting the cyst puncture catheter assembly 70 through the opening in the skull to the area of a cyst is assembled so that the cyst puncture catheter assembly 70 can be inserted stereotactically into the brain and, if desired, placement of the catheter 42 can be observed on a fluoroscopic image or standard radiograph.

Cysts that are encountered in the brain that need to be operated on are typically at least 10 millimeters in cross-section and larger. Many of these cysts can be punctured with the rounded end stylet 30, although some cysts in the brain are of a tougher tissue requiring the use of the pointed end stylet 10.

In performing a puncturing and draining of a cyst in the brain, the first insertion into tissue is with the rounded end stylet 30 inside the catheter 42 until the site of the cyst is reached. Then, the rounded end stylet 30 and catheter 42 are urged against the wall of the cyst to see if it can be punctured without the need for the pointed end stylet 10. If it cannot be punctured, then the rounded end stylet 30 is withdrawn and the pointed end stylet 10 is inserted into the catheter 42. Then, the catheter 42 and stylet 10 are both pushed into the cyst, a distance of at least 5 millimeters to place the openings 60 within the cyst for drainage purposes.

Next, the pointed end stylet 10 is withdrawn from the catheter 42 and a proximal end (not shown) of the catheter 42 is connected to reservoir for collecting the fluids that drain from the cyst through the catheter 42.

It will be understood that the engagement of outer annular shoulders 22 or 38 on the stylet 10 or 30 against the inner annular shoulder 48 inside the catheter distal end portion 40 prevents telescoping of the catheter 42 on the stylet 10 or 30.

In one preferred embodiment of the assembly 70, the smaller-in-diameter lumen 46 is approximately 0.6 mm. in diameter and 2 mm. in length, the angle subtended by the point 20 is approximately 50° the central lumen 44 has a diameter of approximately 1.4 mm. and the catheter 42 has an outer diameter of approximately 2.67 mm., the shaft 12 or 34 has a diameter of approximately 0.55 mm. and a length from the collar 22 or 38 to the pointed end 14 or rounded end 32 of approximately 2 mm. and the collar 22 or 38 has an outer diameter of approximately 1.35 mm.

From the foregoing description, it will be understood that the cyst puncture catheter assembly 70 of the present invention has a number of advantages, some of which have been described above and some of which are inherent to the invention.

Further, it will be understood that modifications can be made to the cyst puncture catheter assembly 70 of the present invention without departing from the teachings of the invention.

Accordingly, the scope of the invention is only to be limited as necessitated by the accompanying claims.

I claim:

1. A catheter and stylet cyst puncture catheter assembly for insertion into the brain, comprising, in combination:

a catheter having a distal portion, a central lumen, an open distal end and a smaller-in-diameter distal end lumen between said central lumen and said open distal end, a first stylet sized to fit within said catheter distal portion, said first stylet comprising an elongate shaft having a blunt distal end and a shoulder extending radially outwardly from said shaft at a location close to said first stylet distal end, and a second stylet sized to fit within said catheter distal portion, said second stylet comprising an elongate shaft having a pointed distal end and a shoulder extending radially outwardly from said shaft at a location close to said second stylet distal end, said distal portion of said catheter having an annular shoulder between said central lumen and said smaller-in-diameter lumen against which said shoulder on said first stylet can seat so that said first stylet and said catheter can be inserted atraumatically together through the brain to a location of a cyst without said catheter moving longitudinally relative to said first stylet and after said catheter has been inserted into the brain at the location of a cyst, said first stylet or said second stylet can be used to puncture a cyst depending on the hardness of the wall of the cyst, said shoulder on said first or on said second stylet seats against said annular shoulder of said catheter so that said blunt end or said pointed end of said first or said second stylet can puncture the wall of the cyst.

2. The assembly of claim 1 wherein said pointed end of said second stylet has the shape of a three or more sided pyramid.

3. The assembly of claim 1 wherein the distance between said shoulder and said tip of said first stylet is between 1 and 4 millimeters.

4. The assembly of claim 1 wherein the distance between said annular shoulder and said open distal end of said catheter is between 1 and 4 millimeters.

5. The assembly of claim 1 wherein said catheter has a distal end which is rounded or tapered from an outer wall surface of said catheter to said open distal end of said catheter.

6. The assembly of claim 5 wherein said distal end of said catheter is tapered at the same angle of the tapered sides of a pyramid shaped pointed tip of said second stylet.

7. The assembly of claim 1 wherein said catheter has at least one opening in a side wall thereof spaced a short distance from said open distal end of said catheter.

8. The assembly of claim 7 wherein said opening is generally oblong in shape.

9. The assembly of claim 8 wherein said opening has a length of approximately 2 millimeters and a width of approximately 1 millimeter.

10. The assembly of claim 7 wherein said catheter distal portion has two opposed openings adjacent said open end of said catheter.

11. The assembly of claim 7 wherein said at least one opening in said wall of said catheter is located between 2 and 6 millimeters from the open end of said catheter.

12. The assembly of claim 10 wherein said opening is located approximately 5 millimeters from said open end of said catheter.

13. A method for inserting a catheter and stylet cyst puncture catheter assembly into the brain to puncture and drain a cyst, the catheter and stylet assembly including, in combination, a catheter having a distal portion, a central lumen, an open distal end and a smaller-in-diameter distal end lumen between said central lumen and said open distal end, a first stylet sized to fit within said catheter distal portion, said first stylet comprising an elongate shaft having a blunt distal end and a shoulder extending radially outwardly from said shaft at a location close to said first stylet distal end, and a second stylet sized to fit within said catheter distal portion, said second stylet comprising an elongate shaft having a pointed distal end and a shoulder extending radially outwardly from said shaft at a location close to said second stylet distal end, said distal portion of said catheter having an annular shoulder between said central lumen and said smaller-in-diameter lumen against which said shoulder on said first or said second stylet can seat, comprising the steps of:

inserting the first stylet and the catheter together through the brain to a location of a cyst without the catheter moving longitudinally relative to the first stylet;

attempting to puncture the cyst with the blunt distal end of the first stylet;

if the first stylet cannot puncture the cyst, removing the first stylet from the catheter while leaving the catheter positioned next to the cyst and then inserting the second stylet into the catheter and puncturing the cyst with the pointed distal end of the second stylet; and, after puncturing the cyst with the first or the second stylet, removing the first or the second stylet from the catheter to drain the cyst.

* * * * *